(12) United States Patent
Reich et al.

(10) Patent No.: US 7,511,816 B2
(45) Date of Patent: Mar. 31, 2009

(54) METHODS AND SYSTEMS FOR DETERMINING DRIFT IN A POSITION OF A LIGHT BEAM WITH RESPECT TO A CHUCK

(75) Inventors: Juergen Reich, San Francisco, CA (US); Yevgeny Kruptesky, San Francisco, CA (US); Christian Wolters, Campbell, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 384 days.

(21) Appl. No.: 11/155,026

(22) Filed: Jun. 16, 2005

(65) Prior Publication Data

US 2006/0285112 A1 Dec. 21, 2006

(51) Int. Cl.
*G01B 11/00* (2006.01)
(52) U.S. Cl. .................................... 356/400
(58) Field of Classification Search ... 356/237.1–237.5, 356/400
See application file for complete search history.

(56) References Cited

U.S. PATENT DOCUMENTS

| | | | | |
|---|---|---|---|---|
| 4,030,835 A | * | 6/1977 | Firester et al. .............. 356/521 |
| 4,119,854 A | * | 10/1978 | Tanaka et al. ............... 250/397 |
| 4,468,120 A | * | 8/1984 | Tanimoto et al. ......... 356/239.8 |
| 4,505,585 A | * | 3/1985 | Yoshikawa et al. ....... 356/237.2 |
| 5,243,195 A | * | 9/1993 | Nishi ......................... 250/548 |
| 5,315,123 A | * | 5/1994 | Itoh et al. ................. 250/492.2 |
| 6,057,921 A | * | 5/2000 | Yao ............................. 356/500 |
| 6,201,601 B1 | | 3/2001 | Vaez-Iravani et al. |
| 6,271,916 B1 | | 8/2001 | Marxer et al. |
| 6,486,964 B2 | * | 11/2002 | Shitamichi .................. 356/614 |
| 6,538,730 B2 | | 3/2003 | Vaez-Iravani et al. |

* cited by examiner

*Primary Examiner*—Tarifur R. Chowdhury
*Assistant Examiner*—Isiaka O Akanbi
(74) *Attorney, Agent, or Firm*—Baker & McKenzie LLP (57) ABSTRACT

Methods and systems for determining drift in a position of a light beam with respect to a chuck are provided. One method includes illuminating a surface with the light beam. The surface has a predetermined position with respect to the chuck during illumination. The method also includes generating signals responsive to the illumination of the surface and determining the drift in the position of the light beam with respect to the chuck using the signals. One system includes an illumination subsystem configured to illuminate a fiduciary with the light beam. The fiduciary has a predetermined position with respect to the chuck during illumination. This system also includes a detector configured to generate signals responsive to the illumination of the fiduciary and a processor configured to use the signals to determine the drift in the position of the light beam with respect to the chuck.

29 Claims, 4 Drawing Sheets

METHODS AND SYSTEMS FOR DETERMINING DRIFT IN A POSITION OF A LIGHT BEAM WITH RESPECT TO A CHUCK

BACKGROUND OF THE INVENTION

1. Field of the Invention

The present invention generally relates to methods and systems for determining drift in a position of a light beam with respect to a chuck. Certain embodiments relate to a method that includes determining drift in a position of a light beam with respect to a chuck on which a specimen is disposed during inspection.

2. Description of the Related Art

The following description and examples are not admitted to be prior art by virtue of their inclusion in this section.

Fabricating semiconductor devices such as logic and memory devices typically includes processing a specimen such as a semiconductor wafer using a number of semiconductor fabrication processes to form various features and multiple levels of the semiconductor devices. For example, lithography is a semiconductor fabrication process that typically involves transferring a pattern to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a semiconductor wafer and then separated into individual semiconductor devices.

Inspection processes are used at various times during a semiconductor manufacturing process to detect defects on wafers. Inspection has always been an important part of fabricating semiconductor devices such as integrated circuits. However, as the dimensions of semiconductor devices decrease, inspection becomes even more important to the successful manufacture of acceptable semiconductor devices. For instance, as the dimensions of semiconductor devices decrease, detection of defects of decreasing size has become necessary since even relatively small defects may cause unwanted aberrations in the semiconductor devices.

Determining the positions of defects on the wafer is also important to facilitate processes such as defect review, during which locations on the wafer at which defects are located are re-visited to generate additional information about the defects. Therefore, if the determined defect locations are inaccurate, the defects must be searched for during review, which will reduce the throughput of the review process. In addition, inaccurate defect locations may reduce the accuracy and usefulness of review if other defects happen to be located at the inaccurate locations thereby confusing the results of inspection and review. Obviously, as the size of defects decreases, the acceptable error in the defect location also decreases. For example, the difficulty of finding defects based on inaccurate defect locations increases as the defect size decreases. Inaccurate defect locations will obviously affect any process that is performed based on defect location information such as defect repair or removal, defect analysis, etc.

One method for increasing the accuracy of defect detection and defect position determination is to accurately calibrate the inspection system prior to inspection of a wafer. For instance, during calibration of an inspection system, the offset of the light beam in the x and y directions from the center of the chuck on which a specimen will be located during inspection may be measured. The measured offset can then be used to correct positional information acquired during the inspection. Therefore, some calibration processes do account for drift in the light beam with respect to the chuck. However, since the calibration processes are typically not performed frequently (e.g., since frequent calibration will reduce throughput), any drift in the position of the light beam between calibrations is not measured. Instead, the incidence light beam position with respect to the chuck is assumed to be relatively stable between calibrations. Therefore, any drift in the position of the light beam between calibrations will produce error in the reported x and y coordinates of defect locations on the wafer.

Some inspection systems that use oblique incidence light beams are configured to account for some variation in the position of the light beam with respect to a wafer. The variation in the position of the light beam with respect to the wafer can be measured during inspection. Such variation is important to measure since variations in height can cause the position of the oblique incidence light beam to change on the wafer. Therefore, systems that can account for variation in the position of the oblique incidence beam due to height variation have provided an important correction for at least part of the drift in the oblique incidence beam position. However, accounting for drift in the x-y positions of the oblique incidence beam as described above only accounts for part of the lateral drift of the beam since a height change produces the same signal as a lateral beam drift requiring twice the radial position correction. As a result, half of the error introduced by drift in the position of the oblique incidence beam is not corrected.

Obviously, the position of a normal incidence light beam will not vary due to height changes. However, the position of the normal incidence beam may vary depending on, for example, drift in the optics of the system and drift in the chuck on which the specimen is located during inspection. The systems described above, however, do not account for any drift in the position of the normal incidence beam between calibrations. Therefore, although a normal incidence beam position will not suffer from positional inaccuracies due to the height variations described above, significant errors may be included in the positional information generated during inspection using a normal incidence beam. Such drift in the optics of the system and the chuck will also affect the positional information generated during inspection with an oblique incidence beam, and such inaccuracies will not be accounted for by the systems described above.

Accordingly, it may be advantageous to develop methods and systems for determining drift in a position of a light beam in the x and/or y directions with respect to a chuck on which a specimen will be disposed during inspection that can account for all possible variations in the position of the light beam with respect to the chuck and that can be performed relatively frequently without substantially reducing throughput of the inspection.

SUMMARY OF THE INVENTION

The following description of various embodiments of systems and methods for determining drift in a position of a light beam with respect to a chuck is not to be construed in any way as limiting the subject matter of the appended claims.

One embodiment relates to a method for determining drift in a position of a light beam with respect to a chuck on which a specimen is disposed during inspection. The method includes illuminating a surface with the light beam. The surface has a predetermined position with respect to the chuck during the illumination of the surface. The method also includes generating signals responsive to the illumination of the surface. In addition, the method includes determining the drift in the position of the light beam with respect to the chuck using the signals.

In one embodiment, the drift includes drift in the position of the light beam with respect to the chuck in the x direction or the y direction. In a different embodiment, the drift includes drift in the position of the light beam with respect to the chuck in x and y directions.

In one embodiment, the surface includes a surface of a fiduciary. In one such embodiment, the fiduciary includes at least one patterned feature. In an additional such embodiment, the fiduciary includes at least one patterned feature having a lateral extent in the y direction and substantially the same characteristics along the lateral extent. In another such embodiment, the fiduciary includes first and second patterned features. In such an embodiment, the first patterned feature extends laterally in the y direction, and the second patterned feature extends laterally in a direction at an angle to the y direction. In a different such embodiment, the fiduciary includes a reflector having a three-dimensional shape. In other embodiments, the surface includes a surface of a detector. In yet another embodiment, the surface includes a surface of a mask positioned in front of a detector.

In another embodiment, the method may be performed between calibrations of an inspection system that includes the light beam and the chuck. In one embodiment, the light beam may be an oblique incidence beam. In a different embodiment, the light beam may be a normal incidence beam.

In one embodiment, the method also includes altering the position of the light beam with respect to the chuck based on the drift. In another embodiment, the method includes determining positions of defects detected on the specimen during the inspection based on the drift. Each of the embodiments of the method described above may include any other step(s) described herein.

Another embodiment relates to a system that is configured to inspect a specimen and to determine drift in a position of a light beam with respect to a chuck on which the specimen is disposed during inspection. The system includes an illumination subsystem configured to illuminate a fiduciary with the light beam. The fiduciary has a predetermined position with respect to the chuck during illumination. The system also includes a detector configured to generate signals responsive to the illumination of the fiduciary. In addition, the system includes a processor configured to use the signals to determine the drift in the position of the light beam with respect to the chuck.

In one embodiment, the drift includes drift in the position of the light beam with respect to the chuck in the x or y direction. In a different embodiment, the drift includes drift in the position of the light beam with respect to the chuck in x and y directions.

In one embodiment, the fiduciary includes at least one patterned feature. In an additional embodiment, the fiduciary includes at least one patterned feature having a lateral extent in the y direction and substantially the same characteristics along the lateral extent. In a further embodiment, the fiduciary includes first and second patterned features. In one such embodiment, the first patterned feature extends laterally in the y direction, and the second patterned feature extends laterally in a direction at an angle to the y direction. In a different embodiment, the fiduciary includes a reflector having a three-dimensional shape.

In some embodiments, the processor is also configured to use the drift to determine positions of defects detected on the specimen by the system. In another embodiment, the processor is configured to use the drift to alter the position of the light beam with respect to the chuck. Each of the embodiments of the system described above may be further configured as described herein.

An additional embodiment relates to a different system that is configured to inspect a specimen and to determine drift in a position of a light beam with respect to a chuck on which the specimen is disposed during inspection. This system includes an illumination subsystem configured to illuminate a detector with the light beam. The detector has a predetermined position with respect to the chuck during illumination. The detector is configured to generate signals responsive to the position of the light beam during the illumination. In addition, the system includes a processor configured to use the signals to determine the drift in the position of the light beam with respect to the chuck.

In one embodiment, the drift includes drift in the position of the light beam with respect to the chuck in the x or y direction. In a different embodiment, the drift includes drift in the position of the light beam with respect to the chuck in x and y directions.

In some embodiments, the detector is not configured for use in the inspection. In an additional embodiment, the system also includes a mask positioned between the illumination subsystem and the detector such that the signals are further responsive to illumination of the mask by the light beam. In one such embodiment, the detector includes a photodiode. Each of the embodiments of the system described above may be further configured as described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "specimen" generally refers to a wafer or any other specimen on which defects of interest may be located. Although the terms "specimen" and "wafer" are used interchangeably herein, it is to be understood that embodiments described with respect to a wafer may configured and/or used for any other specimen as described above.

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

One or more layers may be formed upon a wafer. For example, such layers may include, but are not limited to, a resist, a dielectric material, and a conductive material. Many different types of such layers are known in the art, and the term wafer as used herein is intended to encompass a wafer on which all types of such layers may be formed. One or more layers formed on a wafer may be patterned. For example, a wafer may include a plurality of dies, each having repeatable pattern features. Formation and processing of such layers of material may ultimately result in completed semiconductor devices. As such, a wafer may include a substrate on which not all layers of a complete semiconductor device have been formed or a substrate on which all layers of a complete semiconductor device have been formed.

The wafer may further include at least a portion of an integrated circuit, a thin-film head die, a micro-electro-mechanical system (MEMS) device, flat panel displays, magnetic heads, magnetic and optical storage media, other components that may include photonics and optoelectronic devices such as lasers, waveguides and other passive components processed on wafers, print heads, and bio-chip devices processed on wafers.

Turning now to the drawings, it is noted that FIGS. 1-5 are not drawn to scale. In particular, the scale of some of the elements of the figures is greatly exaggerated to emphasize characteristics of the elements. It is also noted that FIGS. 1-5 are not drawn to the same scale. Elements shown in more than one figure that may be similarly configured have been indicated using the same reference numerals.

Figure 1:
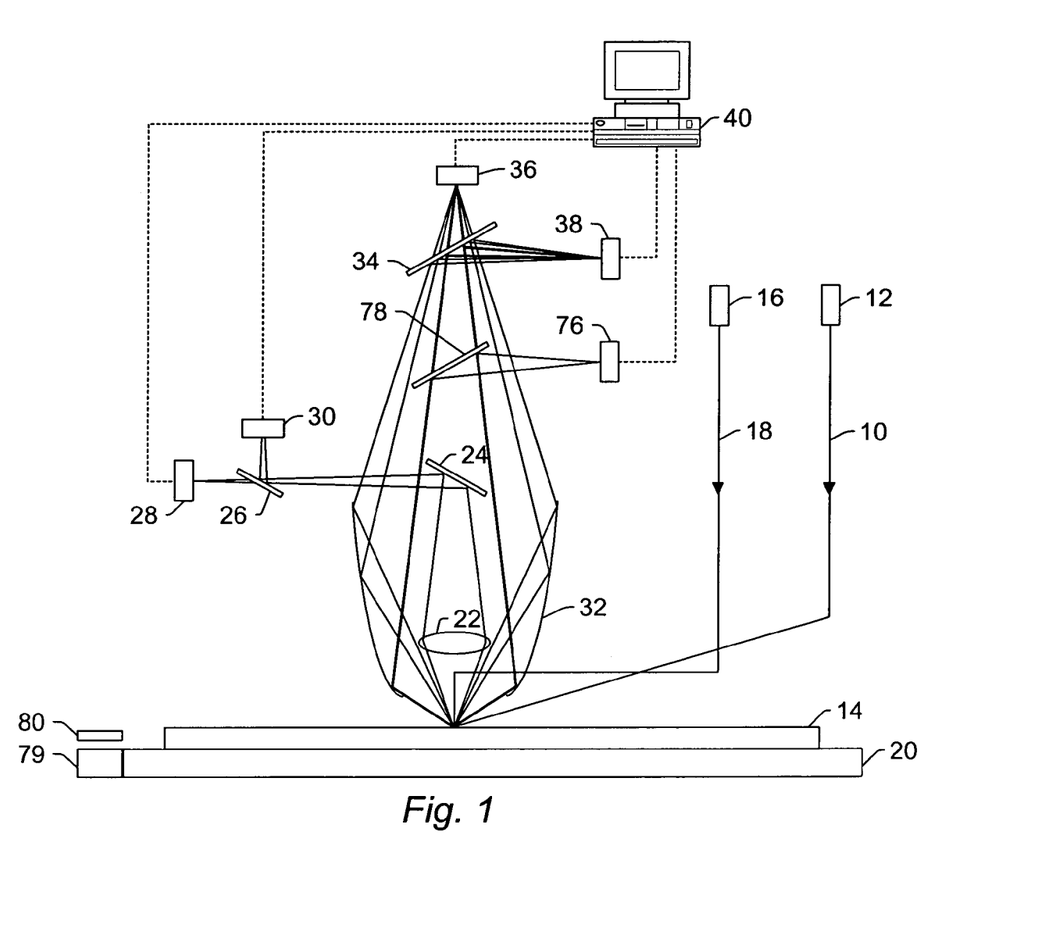
FIG. 1 is a schematic diagram illustrating a cross-sectional view of one embodiment of a system that is configured to inspect a specimen and to determine drift in a position of a light beam with respect to a chuck on which the specimen is disposed during inspection.

One embodiment of a system that is configured to inspect a specimen is illustrated in FIG. 1. The system shown in FIG. 1 is configured for unpatterned wafer inspection and is based on the SP1$^{TBI}$ system, which is commercially available from KLA-Tencor, San Jose, Calif. This inspection system is described in more detail in U.S. Pat. No. 6,538,730 to Vaez-Iravani et al., which is incorporated by reference as if fully set forth herein. The system shown in FIG. 1 may be further configured as described in this patent for patterned and unpatterned wafer inspection. For the sake of clarity, some of the components and details of the system have been omitted from FIG. 1 and the corresponding description presented herein. In addition, U.S. Pat. No. 6,538,730 is related to U.S. Pat. No. 6,201,601 to Vaez-Iravani et al. and U.S. Pat. No. 6,271,916 to Marxer et al., which are also incorporated by reference as if fully set forth herein. The system shown in FIG. 1 may be further configured as described in these patents.

The system shown in FIG. 1 includes an illumination subsystem. The illumination subsystem may be configured to generate light 10. For instance, the illumination subsystem may include light source 12, which is configured to generate light 10. The illumination subsystem is configured to direct light 10 to wafer 14 at an oblique angle of incidence. The illumination subsystem may include a number of optical components (not shown) positioned in a path of light 10 such as folding mirror(s), beam splitter(s), polarizing component(s), filter(s), and lenses. The angle of incidence may vary depending on, for example, the characteristics of the light and the characteristics of the specimen. One suitable angle of incidence may be about 70° from normal to the upper surface of the wafer.

The illumination subsystem also includes light source 16. Light source 16 is configured to generate light 18, which is directed by the illumination subsystem to wafer 14 at a substantially normal angle of incidence. The illumination subsystem may include a number of optical components (not shown) positioned in the path of light 18. These optical components may include any of those described above.

Light sources 12 and 16 may include any suitable light sources known in the art such as lasers. In a different embodiment, the system may include a single light source (not shown) that is used to provide light for both oblique and normal illumination. For example, a single light source such as a multi-wavelength laser may be coupled to a beam splitter (not shown). The beam splitter may be configured to split the light from the laser into separate beams having different wavelengths, one of which is used for normal illumination and the other of which is used for oblique illumination. The illumination subsystem may include any other suitable combination of a single light source and beam multiplier(s) known in the art. In any of the above embodiments, light 10 may have one or more characteristics such as wavelength and/or polarization that are different than the characteristics of light 18. Alternatively, light 10 may have substantially the same characteristics as light 18.

Wafer 14 is supported on chuck 20, which may be rotated and translated such that light 10 and 18 illuminates an area or spot on the wafer that moves in a spiral path. For instance, in this system, a stage provides motion in the x direction. A spindle is mounted to the stage and provides rotation. The chuck is mounted on top of the spindle and supports the wafer. Alternatively, light 10 and 18 may be caused to move over the wafer in any manner known to those skilled in the art to trace the spiral path or another type of scan path across the wafer. Chuck 20 may be further configured as described herein.

Illumination of the wafer will cause scattering of the light from the wafer. In addition, both oblique incidence light and normal incidence light may be scattered from the wafer. The system shown in FIG. 1 includes a detection subsystem that is configured to collect light scattered from the specimen and to generate signals responsive to the scattered light. The signals can be used to detect defects on the specimen as described further herein.

The detection subsystem includes lens collector 22, mirror 24, beam splitter 26, and detectors 28 and 30, which form a "narrow" channel of the detection subsystem. In other words, light scattered from the illuminated area on the wafer along directions relatively close to normal to the surface of the wafer is collected and focused by lens collector 22. In this manner, lens collector 22 collects light scattered from the wafer at relatively "narrow" scattering angles. Lens collector 22 directs the collected light to mirror 24, which directs the light to beam splitter 26. Beam splitter 26 is configured to direct one portion of the light to detector 28 and the other portion of the light to detector 30. One detector may be used to detect light scattered at relatively narrow angles due to illumination by the normal incidence beam, and the other detector may be used to detect light scattered at relatively narrow angles due to illumination by the oblique incidence beam. Detectors 28 and 30 may include any suitable detectors known in the art (e.g., photomultiplier tubes (PMTs)). In addition, detectors 28 and 30 may be similarly or differently configured. The narrow channel portion of the detection subsystem may include any other optical components (not shown) known in the art. For example, one or more polarizing components may be placed in the path of the collected light. In addition, a spatial filter may be included in the narrow channel portion of the detection subsystem to prevent the specular reflection of the normal incidence beam from reaching detectors 28 and 30.

The detection subsystem also includes ellipsoidal mirror 32, beam splitter 34, and detectors 36 and 38, which form a "wide channel" of the detection subsystem. In other words, light scattered from the illuminated area on the wafer along directions relatively far from normal to the surface of the wafer is collected and focused by ellipsoidal mirror 32. In this manner, ellipsoidal mirror 32 collects light scattered from the wafer at relatively "wide" scattering angles. Ellipsoidal mirror 32 directs the collected light to beam splitter 34. Beam splitter 34 is configured to direct one portion of the light to detector 36 and the other portion of the light to detector 38. One detector may be used to detect light scattered at relatively wide angles due to illumination by the normal incidence beam, and the other detector may be used to detect light scattered at relatively wide angles due to the illumination by the oblique incidence beam. Detectors 36 and 38 may include any suitable detectors known in the art (e.g., PMTs). In addition, detectors 36 and 38 may be similarly or differently configured. The wide channel portion of the detection subsystem may include any other optical components (not shown) known in the art. For example, one or more polarizing components may be placed in the path of the collected light.

Detectors 28, 30, 36, and 38 are configured to generate signals responsive to the scattered light. Processor 40 is coupled to detectors 28, 30, 36, and 38 by transmission media as shown by the dotted lines in FIG. 1. The transmission media may include any suitable transmission media known in the art. In addition, one or more additional components (not shown) may be interposed between the detectors and the processor such as analog-to-digital converters. In this manner, signals generated by the detectors can be sent to the processor. The processor may be configured to use the signals to detect defects on the wafer. The processor may also be configured to use any algorithm or method known in the art for detecting the defects using the signals.

The system shown in FIG. 1 may include one or more components (not shown) that are configured to position the oblique incidence beam with respect to the surface of the wafer. In this manner, the processor may also use information from these beam positioning component(s) to correct the positional information generated during inspection. However, as described above, since these component(s) are configured to determine errors in the position of the oblique incidence beam with respect to changes in height, the positional error of the oblique incidence beam with respect to the chuck is only partially corrected. In addition, such a system does not include any measurement of or correction for the position of the normal incidence beam with respect to the chuck. Instead, after x-y calibration of the normal and oblique incidence beams, the positions of the beams with respect to the chuck are assumed to be stable.

The system shown in FIG. 1, however, can be modified such that the system is configured to determine drift in a position of a light beam with respect to the chuck on which the specimen is disposed during inspection. The modified system can, therefore, determine x and/or y positions of defects on a wafer more accurately. One part of the correction of the defect positions relies on determining the drift of the incidence beam spot relative to a predetermined position on the chuck such as the center of the chuck at which a spindle is located for rotating chucks. The system embodiments described herein improve this part of the x and/or y correction of defect locations by measuring drifts in the position of the incidence beam between calibrations.

Figure 2:
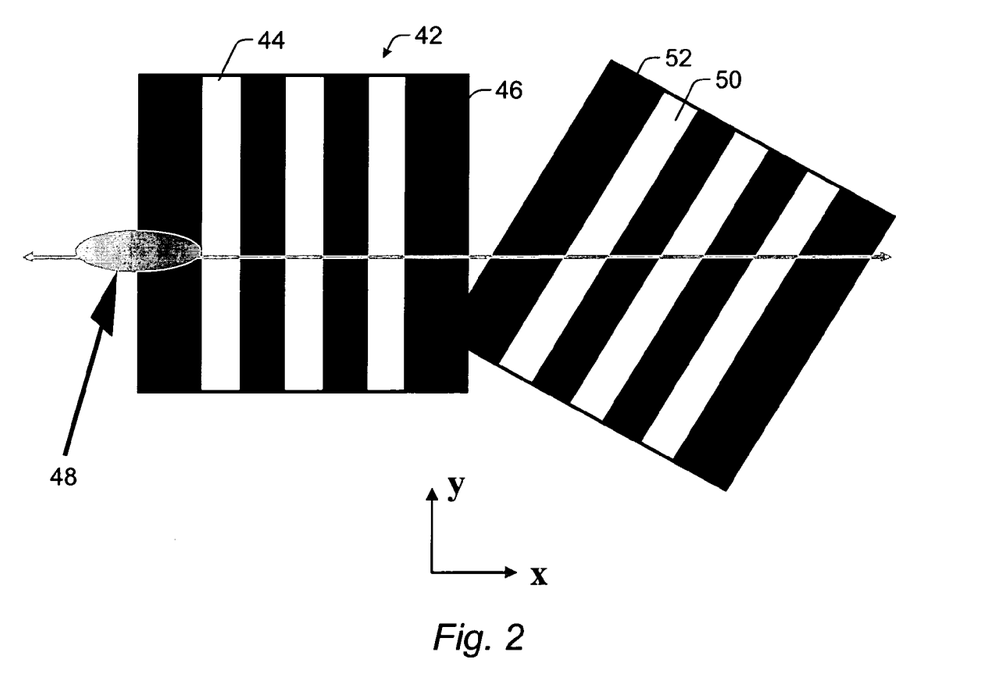
FIG. 2 is a schematic diagram illustrating a top view of one embodiment of a fiduciary.

In one such embodiment, the system shown in FIG. 1 may be configured to include a fiduciary (not shown in FIG. 1) having a predetermined position with respect to the chuck. The fiduciary can be used to determine drift in a position of the light beam with respect to the chuck as described further herein. FIG. 2 illustrates one embodiment of such a fiduciary. In this embodiment, fiduciary 42 includes at least one patterned feature 44. The fiduciary includes at least one patterned feature such that light scattering from at least one feature can be used to determine drift in a position of the light beam with respect to the chuck as described further herein. In addition, although one pattern feature is sufficient for determining and correcting drift in the position of the light beam in one direction, the fiduciary may include more than one patterned feature to determine and correct drift in the x and y directions and/or to provide better accuracy in the drift measurements (e.g., through averaging).

Although the fiduciary is shown in FIG. 2 to include three patterned features, it is to be understood that the fiduciary may include fewer or more than three patterned features. Furthermore, although the features of the fiduciary are shown in FIG. 2 to be relatively "even," it is to be understood that the feature(s) of the fiduciary do not have to be as even as shown in FIG. 2.

As shown in FIG. 2, patterned features 44 include trenches formed in material 46. In one example, material 46 is black anodized aluminum, and the trenches are substantially linear and substantially parallel scratches formed in the black anodized aluminum, which expose the blank aluminum. In another example, material 46 is a piece of a bare silicon wafer, and the trenches are grooves cut into the surface of the silicon wafer with a high power laser. However, such patterned features may be formed in any suitable material known in the art using any suitable process known in the art. In addition, the patterned features may have any shape that, when illuminated, will cause characteristic light scattering. The patterned features and the material may also be formed of dissimilar materials. For example, the patterned features may include a set of lines formed on a piece of a silicon wafer. The lines may be formed of a material other than silicon such as a conductive material, a dielectric material, or a photoresist.

As shown in FIG. 2, the patterned feature(s) of fiduciary 42 have a lateral extent in the y direction. In this manner, the patterned feature(s) are aligned perpendicularly to the stage travel direction (the x direction). In one such embodiment, the patterned feature(s) have substantially the same characteristics along the lateral extent in the y direction. The characteristics of the patterned feature(s) that are substantially the same along the lateral extent of the feature(s) may include any characteristics that may affect the light scattered from the feature(s), which is used to determine drift in the position of the light beam with respect to the chuck as described further herein. In a different embodiment, the patterned feature(s) may have different characteristics along their lateral extent. In such an embodiment, the characteristics of the patterned feature(s) along their lateral extent may be characterized prior to use of the fiduciary. In this manner, any variations in the characteristics may be used to correct the light scattering signals, which are used to determine drift in the position of the light beam with respect to the chuck. As such, the variations in the characteristics of the patterned feature(s) will not cause error in the determined drift in the position of the light beam.

As shown in FIG. 2, patterned feature(s) 44 of fiduciary 42 are illuminated by light beam 48 of the system. The patterned feature(s) are configured such that one patterned feature 44 is illuminated by light beam 48 at a time. In other words, the size and spacing of the patterned feature(s) may be selected based on the spot size of the incidence beam(s) of the system such that one patterned feature is illuminated by the incidence beam(s) at a time. In one example, the width of the patterned feature(s) may be less than or equal to about half of the dimension of the spot size in the direction in which the light beam is caused to move over the fiduciary. For example, if the dimension of the spot size in the direction in which the light beam is caused to move over the fiduciary is about 60 micron, then the width of the patterned feature(s) may be about 20 micron or about 30 micron. In addition, the spacing between the patterned features (if the fiduciary includes more than one patterned feature) may be larger than the beam width such that only one feature is illuminated by the beam at a time. In this manner, in the simplest use case, one feature having a size much smaller than the beam diameter may be illuminated. The size and spacing of the patterned feature(s) may vary depending on the spot size of the light beam in addition to other characteristics of the system (e.g., resolution, pixel size, etc.). Therefore, an appropriate configuration for the patterned feature(s) of the fiduciary preferably varies depending on the characteristics of the system in which it will be used. In addition, although light beam 48 is shown in FIG. 2 to have a generally ellipsoidal shaped spot on the fiduciary, it is to be understood that the light beam may have any appropriate shape (e.g., circular) known in the art.

In this manner, the light scattering signals generated by illuminating the fiduciary will contain light scattering from the patterned feature. Since the patterned feature will have a predetermined position within the fiduciary, and since the fiduciary has a predetermined position with respect to the chuck during illumination as described further herein, signals corresponding to the light scattered from the patterned feature due to illumination by light beam 48 can be used to determine drift in the position of the light beam with respect to the chuck.

The patterned feature that is illuminated by the light beam may include all light scattering artifacts of the patterned feature such as top edges and bottom edges. However, in some embodiments, the patterned feature that is illuminated by the light beam may include only a portion of one patterned feature. For instance, the patterned feature that is illuminated may include only one top edge of one patterned feature. In other words, the patterned feature that is illuminated to acquire data responsive to drift in the position of the light beam with respect to the chuck may include any one artifact of one patterned feature that will affect the light scattered from the fiduciary in a measurable manner.

As further shown in FIG. 2, fiduciary 42 may include, in some embodiments, two patterned features. Patterned feature 44 formed in material 46 is one of the patterned features. As described above, patterned feature 44 extends laterally in the y direction. Patterned feature 50 formed in material 52 is the second of patterned features. Patterned feature 50 and material 52 may include any of the patterned feature and material examples described above. In addition, patterned features 44 and 50 may be similarly configured. Materials 46 and 52 may also be similarly configured.

As shown in FIG. 2, patterned feature 50 extends laterally in a direction at an angle to the y direction. In one embodiment, the direction in which patterned feature 50 extends may be about 45° from the y direction. However, the direction in which patterned feature 50 extends may be at an angle between greater than 0° and less than or equal to 90° from the y direction. In this manner, the light scattering from the first patterned feature may be used to determine drift in the beam position with respect to the chuck in one direction, and the difference between the light scattering from the first and second patterned features may be used to determine drift in the beam position with respect to the chuck in another direction as described further herein.

Figure 3:
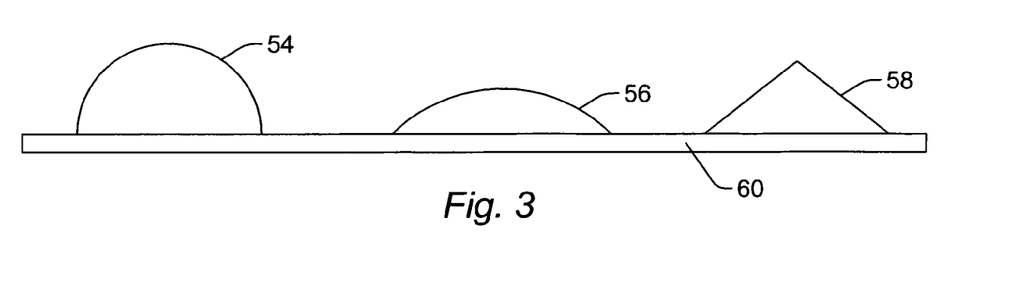
FIG. 3 is a schematic diagram illustrating a cross-sectional view of different embodiments of a fiduciary.

In other embodiments, the fiduciary may include a reflector having a three-dimensional shape. FIG. 3 illustrates several embodiments of such a fiduciary. As shown in FIG. 3, fiduciary 54 is a reflector having a partial spherical shape. Fiduciary 56 is also a reflector having a partial spherical shape. Fiduciaries 54 and 56 have different curvatures. Such reflectors may also advantageously magnify the light reflected from the fiduciary. As further shown in FIG. 3, fiduciary 58 is a reflector having a generally conical shape. Although two differently shaped reflectors that can be used as a fiduciary are shown in FIG. 3, it is to be understood that a reflector having any shape that reflects light at different angles depending on the position of the incident light beam on the reflector may be used as a fiduciary. An appropriate shape for the reflector may also vary depending on characteristics of the system such as angle of incidence and angle of collection. In addition, each of the fiduciaries shown in FIG. 3 may be formed of any suitable reflecting material such as aluminum. In addition, an appropriate material for such a reflecting fiduciary may be selected based on characteristics of the light beam such as wavelength and polarization.

As shown in FIG. 3, each of the fiduciaries may be coupled to substrate 60. The substrate may include, for example, a portion of a silicon wafer or another material that facilitates coupling of the fiduciary to the chuck in a manner as described further herein. Instead, each of the fiduciaries may be coupled directly to the chuck or a device coupled to the chuck (e.g., a spindle of a rotating chuck). In addition, the fiduciary included in the system may include only one reflector having a three-dimensional shape. Alternatively, the fiduciary may include more than one reflector, each of which has a different three-dimensional shape or the same three-dimensional shape but with different characteristics (e.g., curvature, height, etc.).

As described above, therefore, the fiduciary is configured to either scatter or reflect the light beam that illuminates the fiduciary. However, in other embodiments, the fiduciary may be configured such that the light beam is transmitted through the fiduciary to create a transmitted light response, which can be used as described herein to determine drift in the position of the light beam with respect to the chuck in the x and/or y directions. The positions of the fiduciary and detector(s) used for beam position drift measurements based on transmitted light will be different than those used for beam position drift measurements based on scattered or reflected light. However, the positions of a transmission-based fiduciary and the detector(s) can be determined based on the characteristics of the system and the fiduciary as generally described further herein.

Figure 4:
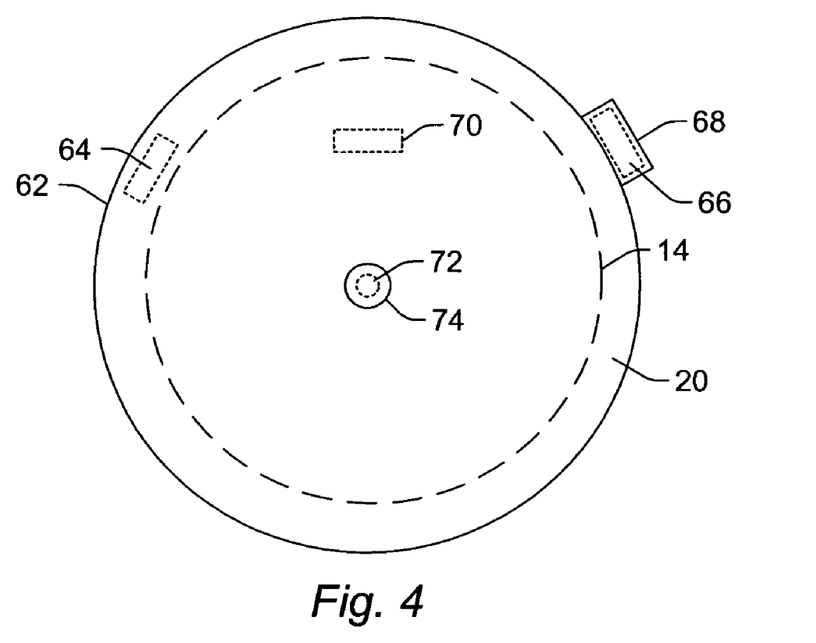
FIG. 4 is a schematic diagram illustrating a top view of a chuck and different embodiments of predetermined positions of a fiduciary with respect to the chuck.

FIG. 4 illustrates different manners in which a fiduciary such as those described above may be coupled to a chuck of the system shown in FIG. 1. As shown in FIG. 4, specimen 14 is disposed on chuck 20 during inspection. As further shown in FIG. 4, specimen 14 has an area that is smaller than that of chuck 20. Chuck 20 is often configured to have an area that is larger than the area of specimen 14 such that even if the location of the specimen on the chuck varies, the specimen can be wholly supported by the chuck. Chuck 20 may typically have a radius that is greater than the radius of the specimen by a few millimeters. Therefore, since the fiduciaries described herein are relatively small in size, a fiduciary may be positioned near edge 62 of chuck 20 in an area upon which the specimen will not be disposed during inspection. For example, as shown in FIG. 4, a fiduciary may be positioned in location 64 on chuck 20 between edge 62 and the outer edge of specimen 14. The fiduciary may be coupled to the chuck using an adhesive, a mechanical device, or any other suitable coupling mechanism known in the art.

In a different embodiment, a fiduciary may be positioned in location 66, which is external to the area of chuck 20. In this embodiment, the fiduciary may be coupled to support 68, which may or may not be attached to the chuck using any coupling mechanism known in the art. In this manner, the support and the fiduciary located on the support may or may not rotate with the chuck. Support 68 may have dimensions that are greater than or equal to the dimensions of the fiduciary. In addition, support 68 may have an area that is sufficient to adequately support the fiduciary but which will not interfere with movement of the chuck within the system. For instance, the support preferably has dimensions that allow adequate clearance between the support and all other components of the system if it moves with the chuck.

In another embodiment, a fiduciary may be located within an area of the chuck on which a specimen will be disposed during inspection. For instance, a fiduciary may be positioned in location 70, which is spaced from the center of the chuck and under a specimen during inspection. In another example, a fiduciary may be positioned in location 72 at approximately the center of the chuck. In this manner, the fiduciary may be attached to spindle 74, which may be coupled to the chuck to provide rotation of the chuck during inspection.

The fiduciary may be positioned in locations 70 and 72 such that the fiduciary does not locally alter a position of the specimen during inspection. For example, the fiduciary may be "sunk" into the chuck such that the upper surface of the fiduciary is approximately flush with the upper surface of the chuck. In another example, the fiduciary may be sunk into the chuck during inspection of a specimen and may be moved to a height above the upper surface of the chuck during measurement of the beam position drift such that the fiduciary is approximately located in the object plane of the system. In this manner, the fiduciary may be located roughly in the focus of the light beam. Such movement of the fiduciary may be performed using any suitable device and controller known in the art.

In another embodiment, the fiduciary may be attached to another device (not shown) coupled to the chuck. For example, some chucks may be coupled to one or more holders that are used for holding calibration devices. For instance, the SP1 and SP2 inspection systems, which are commercially available from KLA-Tencor, include a holder for an "Autocal" pin, which is mounted next to the chuck and is used to calibrate the characteristics of detectors of the system such as gain. Such a holder or a similarly configured holder can be used for attachment of the fiduciary to the chuck.

Although several different locations in which a fiduciary can be positioned with respect to a chuck are shown in FIG. 4, it is to be understood that the fiduciary may have any location with respect to the chuck. In addition, the position of the fiduciary with respect to the chuck may not change due to motion of the chuck. Instead, the fiduciary may rotate and/or translate or otherwise move with the chuck. In addition, the position of the fiduciary may be altered depending on whether or not a beam position drift measurement is being performed. For instance, the system could be configured to flip the fiduciary in and out of position as long as the position of the fiduciary with respect to the chuck is relatively reproducible. In any of the above examples, the fiduciary has a predetermined position with respect to the chuck at least during illumination of the fiduciary.

The system also includes an illumination subsystem that is configured to illuminate the fiduciary with the light beam. The illumination subsystem preferably includes the illumination subsystem that will be used for inspection such that the drift in the position of the light beam with respect to the chuck in the x and/or y directions can be determined using the fiduciary. The light beam that illuminates the fiduciary may include any of the light beams that will be used for inspection. For instance, in the system of FIG. 1, the light beam that illuminates the fiduciary may include oblique incidence beam 10 or normal incidence beam 18. In addition, two or more such light beams may illuminate the fiduciary sequentially or simultaneously. In this manner, the drift in the position of two or more light beams may be determined sequentially or simultaneously.

As shown in FIG. 4, the fiduciary may be located in a position with respect to the chuck which is not normally illuminated by the illumination subsystem. In particular, locations 64 and 66 are positioned in areas in which a specimen is not normally disposed. Therefore, the system may not be configured to illuminate locations 64 and 66. However, relatively simple changes to the illumination control subsystem and/or software of the system may be made such that the illumination subsystem can illuminate these and any other location in which a fiduciary is located during measurement of drift in the x and/or y positions of the light beam with respect to the chuck. Appropriate changes to the illumination control subsystem and/or software will be obvious to one of ordinary skill in the art and will depend on the location of the fiduciary.

The system also includes a detector that is configured to generate signals responsive to illumination of the fiduciary. In one embodiment, the detector may include one of the detectors of the system that will be used to perform inspection of the specimen. For example, in the embodiment of FIG. 1, the detector that is used to generate signals responsive to illumination of the fiduciary may include detector 28, 30, 36, or 38. In addition, if the system includes more than one detector as shown in FIG. 1, two or more detectors may generate signals responsive to illumination of the fiduciary, and the signals from the two or more detectors may be used as described further herein to determine drift in the position of the light beam with respect to the chuck in the x and/or y directions. However, it is to be understood that even if the system includes more than one detector, signals from only one of the detectors are sufficient for the beam position drift measurements described herein.

In other embodiments, the system may include an additional detector that is not used for inspection. Instead, the additional detector may only be used for determining drift in a position of the light beam with respect to the chuck in the x and/or y directions. In one embodiment, as shown in FIG. 1, the system may include detector 76. During illumination of the fiduciary, beam splitter 78, which is located in the path of the light collected from the fiduciary, directs light to detector 76. Since beam splitter 78 directs only a portion of the light collected by ellipsoidal mirror 32 to detector 76, beam splitter 78 may also be positioned as shown in FIG. 1 during inspection of a specimen since the reduction in the collected light transmitted to detectors 36 and 38 may not be substantial. However, in other embodiments, beam splitter 78 may be moved into and out of the path of the collected light depending on whether inspection or measurement of the light beam position drift is being performed. Beam splitter 78 may be moved into and out of the collected light path using any device and controller known in the art.

Detector 76 may be further configured as described herein and may vary depending on the configuration of the fiduciary. For instance, in an embodiment where the fiduciary includes a patterned feature, the detector may include a PMT or any other detector that can detect a scattering response during illumination of the fiduciary. If the fiduciary is a reflector having a three-dimensional shape, the detector is preferably configured to detect variations in the angle at which light is reflected from the fiduciary during illumination of the fiduciary. Such a detector may include, for example, a quad-cell detector, a charge coupled device (CCD) camera, a time delay integration (TDI) camera, an array of photodiodes, a phosphorous screen, or any other appropriate position sensitive detector known in the art.

As shown in FIG. 1, detector 76, like detectors 28, 30, 36, and 38, is coupled to processor 40 by a transmission medium shown by the dotted line. The transmission medium may include any suitable transmission medium known in the art. Processor 40 is configured to use signals generated by at least one of the detectors that are responsive to illumination of the fiduciary to determine drift in the position of the light beam in x and/or y directions with respect to the chuck. In particular, drift in the position of the light beam in the x and/or y directions can be determined with respect to a predetermined position on the chuck (e.g., a spindle center).

For example, a drift in the light beam position may be detected as an apparent shift in the scattering pattern response measured by the detector(s). In one such example, when the light beam illuminates the fiduciary, the scattering pattern is recorded by the detector(s) described above while the chuck position for each data sample is also recorded. The chuck position may be recorded using any device or method known in the art. In this manner, the processor can use the positional information in the scattering response measured by the detector(s) and the recorded chuck position to determine drift in the position of the light beam with respect to the chuck. For example, the processor may compare the measured scattering patterns versus chuck position from measurement to measurement in order to extract the light beam position drift.

As described above, the patterned features are preferably configured such that one patterned feature can be illuminated at a time. As such, the scattering response will be the convolution of the beam profile and the scattering power of the patterned feature. In addition, although movement in the light beam may cause most of the drift in the position of the light beam with respect to the chuck, the systems described herein can be used to measure and correct any relative shift of the position of the light beam with respect to a position on the chuck (e.g., a spindle center) independent of whether the relative shift in the light beam position is caused by drifts in the beam or mechanical drifts of the chuck (e.g., the spindle).

In addition, arrangement of patterned features of the fiduciary perpendicular and at angles between 0° and 90° to the relative motion of the stage allows measurement of beam drifts parallel and perpendicular to the direction of travel. For example, as further described above, at least one patterned feature of the fiduciary may be aligned perpendicularly to the stage travel direction (e.g., the x direction). Therefore, the scattering response measured during illumination of these feature(s) of the fiduciary can be used to determine the light beam position drift in the stage travel direction, which may be the direction in which the largest drifts in the light beam position may be observed. In addition, as described above, at least one patterned feature of the fiduciary may be oriented at an angle to the stage travel direction. Therefore, the differences in the apparent pattern shifts of the perpendicular and angled patterned feature(s) can be used to determine drifts in the light beam position in the direction perpendicular to the stage travel direction (e.g., the y direction).

As described further above, the patterned feature(s) may have substantially uniform characteristics across their lateral extents such that the characteristics of the patterned feature(s) in this direction will not change the shape of the scattering response, which in turn could appear as a beam drift in the direction perpendicular to the patterned features. However, as described above, the patterned feature(s) may not have substantially uniform characteristics along their lateral extents as long as the variations in the characteristics are known. In this manner, the processor may use these known variations to alter the measured scattering response prior to determining drift in the position of the light beam with respect to the chuck in the x and/or y directions. Alternatively, if the beam drift is determined as a difference between scattering responses measured at different times, the variations in the scattering responses due to variations in the characteristics of the patterned feature (s) may "cancel out" thereby eliminating any error in the light beam position drift measurement due to the variations in the characteristics.

As described above, the system shown in FIG. 1 is configured to illuminate a specimen with an oblique incidence beam as well as a normal incidence beam. In such a system, drift in the positions of the oblique and normal incidence beams with respect to the chuck in the x and/or y directions may be detected sequentially or simultaneously. For example, only one beam may be used to illuminate the fiduciary at a time for sequential measurements of beam position drift. In another example, the detector may be configured to detect scattering of both light beams from the fiduciary at the same time and to generate different signals for the light scattering of each of the light beams. In this manner, drift in the position of more than one light beam may be measured simultaneously.

In addition, as described further above, drift in the position of the oblique incidence beam on the wafer may vary depending on height changes. Therefore, during inspection of a specimen with the oblique incidence beam, the beam position may be monitored with beam positioning components to correct for drift in the position of the oblique incidence beam on the specimen due to height changes. As described further above, such correction of the beam position due to height changes can only correct part of the beam position drift. Therefore, such beam positioning components may be used in combination with the beam position drift measuring components described herein to correct the remaining half of the error introduced by a beam position drift. In this manner, the systems described herein can be used to correct all variations in the position of the light beam with respect to the wafer and the chuck, which may be caused by height changes, drift in the optics, and drift in the position of the chuck.

The system may be configured such that at selected times the light beam illuminates the fiduciary while the detector(s) of the system detect the light scattered or reflected from the fiduciary. For instance, illumination of the fiduciary may be first performed at the same time as the x y calibration of the system. Subsequently, light beam position drift can be measured by cross-correlating newly measured scattering patterns to the one recorded at the x y calibration. The beam position drift can then be combined with the beam position offset determined during calibration to determine the position of the light beam with respect to the chuck in x and/or y directions. The beam position drift can be measured before each inspection performed by the system or at other selectable intervals.

In some embodiments, the processor is also configured to use the determined drift in the position of the light beam to determine positions of defects detected on the specimen by the system. In this manner, the processor may be configured to correct positions of defects based on the drift in the position of the light beam, which was used for the inspection. In another embodiment, the processor is configured to use the drift in the position of the light beam to alter the position of the light beam with respect to the chuck. In this manner, the processor may be configured to correct the position of the light beam with respect to the chuck before an inspection is performed.

The system embodiments described herein, therefore, have several advantages over other systems configured to inspect a specimen. For example, one of the main purposes of a defect inspection system is to provide not just the number of detected defects but also x and y coordinates of each defect in order to allow review of the defects with microscopes. As sensitivity to smaller and smaller defects is required, the demand for better accuracy of the x and y coordinates is also increased. However, light beam position drifts can negatively affect the accuracy of the x and y defect coordinates to the extent that x and y calibration would be required before every inspection that is to be used for review. In addition, many users expect to be able to perform defect review using any data acquired by a defect inspection system. Therefore, the frequent x and y calibration needed to allow review of defects detected in every inspection would obviously substantially reduce the throughput and the value of the defect inspection system.

The systems described herein, however, provide measurement of drift in the position of an incident light beam of a wafer inspection system between calibrations to improve the accuracy of the x and y coordinates of defect positions. In addition, since the systems described herein can measure and/or correct drift in the light beam position with respect to the chuck in the x and/or y directions relatively quickly, frequent measurement and/or correction of drift in the light beam position will not substantially reduce the throughput and the value of the system. Furthermore, since the systems described herein can be used to measure drift in the incident light beam position regardless of the cause of the drift (e.g., drift in the optics, drift in the chuck position, change in the height, etc.), the systems described herein can provide much more accurate x and y coordinates of detected defects than other systems that account for only part of the drift in the incident light beam.

The systems described herein can also be advantageously used to measured and/or correct drift in the position of one or more light beams in unpatterned specimen inspection systems. For instance, in some inspection systems configured for inspection of patterned specimens such as patterned reticles or patterned wafers, the inspection systems may use patterns or alignment marks formed on the specimens themselves to determine positional information about the data acquired during inspection with respect to the patterns or alignment marks. However, since an unpatterned specimen will have no such patterns or alignment marks, these systems cannot be used to correct drift in the position of a light beam or defect positional information for unpatterned specimen inspection. In addition, although these systems may be useful for determining drift in a position of the light beam with respect to the pattern or alignment marks, since the actual location of the pattern and the alignment marks may vary somewhat depending on alignment error in the process used to form the pattern or the alignment marks, these systems will be unsuitable for determining drift in the light beam with respect to a chuck. Error in such drift measurements using a pattern or alignment mark on the specimen may also be caused by variation in the actual position of the wafer on the chuck. As such, the systems described herein provide capability for different light beam position drift measurements than other currently used systems.

The substantially accurate defect positions determined by the systems described herein can also be advantageously used in any other process that relies on defect positions to carry out the process on the specimen. For instance, the defect position information generated as described herein can be used in a repair process in which individual defects are located and repaired based on the defect position determined by inspection. In an additional example, the defect position information determined as described herein can be used in a defect removal process such as a cleaning process in which individual defects are located and removed based on the determined positions. In another example, the defect position information determined as described herein can be used in an analysis process in which individual defects are located based on the defect position information such that analysis (e.g., composition analysis) can be performed on individual defects. In any case, the defect position information may be sent from the systems described herein (e.g., by processor 40) to a system used to carry out such processes. These systems can then use the inspection data to carry out the processes.

Another embodiment relates to a different system that is configured to inspect a specimen and to determine drift in a position of a light beam with respect to a chuck on which the specimen is disposed during inspection. This system includes an illumination subsystem that is configured to illuminate a detector with the light beam. The detector has a predetermined position with respect to the chuck during illumination. The illumination subsystem and the chuck may be configured as described above. The detector is configured to generate signals responsive to the position of the light beam during the illumination. In other words, the detector may include a position sensitive detector. In addition, the system includes a processor that is configured to use the signals to determine the drift in the position of the light beam with respect to the chuck in x and/or y directions. The processor may be further configured as described herein.

This system is, therefore, substantially similar to the system embodiments described above except that this system does not include a fiduciary as described above. Instead, in this system, the detector directly measures the position of the light beam with respect to the chuck in the x and/or y directions. For instance, the detector may be configured to generate signals that are responsive to drift in the position of the light beam on the photosensitive area of the detector. In addition, the detector preferably has a predetermined position with respect to the chuck such that drift in the position of the light beam with respect to the detector can be used to determine drift in the position of the light beam with respect to the chuck in the x and/or y directions. In one such embodiment, the detector may include a two-dimensional array of photosensitive elements such as photodiodes. Therefore, the positions of the diodes on which the light beam impinges can be recorded and used to determine drift in the position of the light beam with respect to the detector.

Although one example of a detector that can be used for directly measuring drift in a position of a light beam is provided above, it is to be understood that the detector may include any position sensitive detector that can measure a position of a light beam impinging thereon. Additional examples of such detectors include, for example, a CCD camera, a TDI camera, a quad cell detector, a phosphorous screen, and any other position sensitive detector known in the art. In addition, in such embodiments, it may be preferable to use a detector that is not configured for use in the inspection. For instance, the detectors used for inspection may be located in positions that are generally unsuitable for measuring a position of a beam with respect to the detector. Therefore, in such a system, additional detector 79 shown in FIG. 1 may be used for measuring drift in the position of the light beam with respect to the detector and therefore for determination of the drift of the position of the light beam with respect to the chuck in the x and/or y directions. Although one position for detector 79 is shown in FIG. 1, it is to be understood that the detector may be located in any of the positions of the fiduciary described above.

In the embodiments described above, therefore, the detector may be used to directly measure the position of the light beam with respect to the chuck by directly measuring the position of the light beam with respect to the detector. In other embodiments, however, the system may include a mask positioned between the illumination subsystem and the detector such that the signals generated by the detector are responsive to illumination of the mask by the light beam. In such embodiments, the detector may include a position insensitive detector. One such embodiment of a mask is shown in FIG. 1. In particular, mask 80 is positioned between the illumination subsystem and detector 79. In this manner, the signals generated by the detector will be responsive to illumination of the mask.

Figure 5:
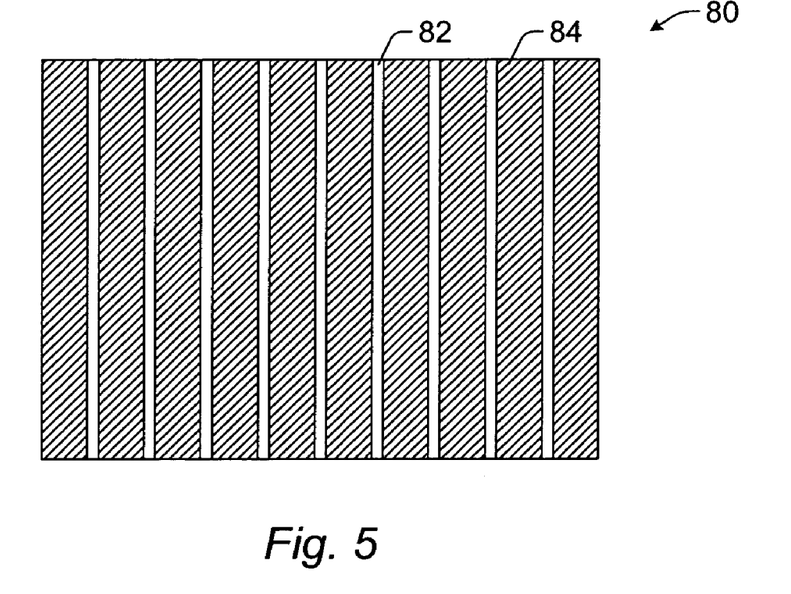
FIG. 5 is a schematic diagram illustrating a cross-sectional view of one embodiment of a mask that can be positioned between an illumination subsystem and a detector.

One embodiment of mask 80 is shown in cross-section in FIG. 5. As shown in FIG. 5, mask 80 includes at least one slit 82 formed in material 84. Slit(s) 82 are configured to transmit light while material 84 is selected such that light is not substantially transmitted through the material (or such that at least significantly less light is transmitted through the material than the slits). In this manner, during illumination of mask 80, a response will be measured by detector 79 similar to the scattering response that is generated by illuminating a fiduciary that includes patterned feature(s) as described above. However, the detector will measure light transmitted through the mask. In this manner, the mask may essentially function as a transmitting fiduciary. The feature(s) of the mask may be configured as described above with respect to the patterned feature(s) of the fiduciary. For instance, the mask may include two slits (although one slit may be sufficient) (not shown), one slit that is arranged in a direction perpendicular to the stage travel direction, and another slit that is arranged in a direction at an angle to the stage travel direction. In another example, the slit(s) may have substantially the same characteristics along the lateral extent of the slit(s). Furthermore, although the feature(s) of the mask are shown in FIG. 5 to be relatively "even," it is to be understood that the feature(s) of the mask do not have to be as even as shown in FIG. 5.

The mask preferably includes at least one slit. However, as shown in FIG. 5, the mask may include more than one slit. Furthermore, although the mask is shown in FIG. 5 to include slits, it is to be understood that the mask may include any feature(s) that will cause a transmitted light response that will change depending on the position of the light beam that illuminates the mask. Therefore, the response that is measured during illumination of the mask may be used to determine drift in a position of the light beam with respect to the chuck in the x and/or y directions as described further above.

In one such embodiment, light transmitted by mask 80 may be detected by a detector such as a relatively large photodiode (e.g., a photodiode having dimensions on the order of several millimeters or more). In addition, the detector may not be used for inspection. Using a detector for beam position drift measurements that is not used for inspection may be advantageous in that the detector can be set up independently of the detectors used in the wafer inspection, and any effects of the beam position drift measurements on the actual wafer inspection measurements can be avoided. The embodiments of the systems described above (which do not include a fiduciary) will have the same advantages as other system embodiments described herein.

Although the embodiments are described above with respect to one configuration of a wafer inspection system, it is to be understood that any wafer inspection system known in the art regardless of chuck configuration, detector configuration, and illumination configuration may be modified or configured as described herein. In addition, the systems described herein may be implemented on inspection systems other than wafer inspection systems (e.g., reticle inspection systems) to provide more accurate defect position determination for other types of inspection systems. Furthermore, the systems described herein may be implemented on systems other than inspection systems such as metrology systems that are configured to perform measurements on wafers or other specimens to provide more accurate measurements as a function of position on the specimen. Moreover, the system configurations described herein may be used in any apparatus to track long term light beam position drift.

Figure 6:
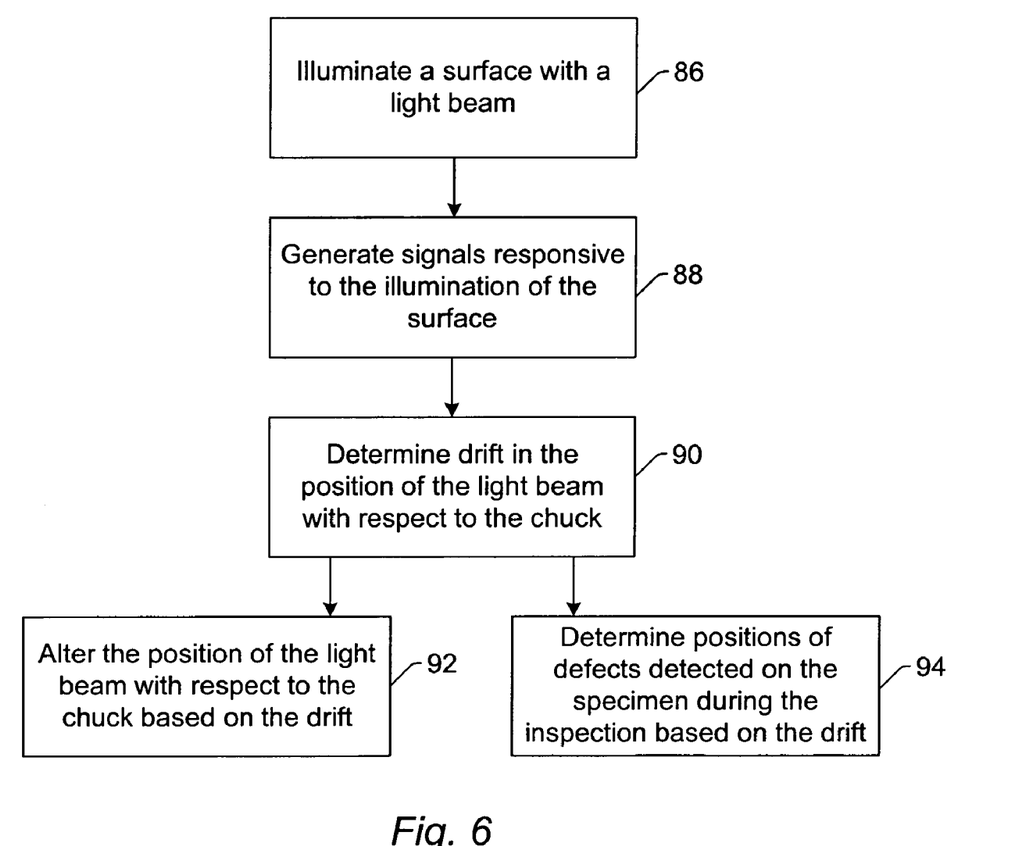
FIG. 6 is a flow chart illustrating one embodiment of a method for determining drift in a position of a light beam with respect to a chuck on which a specimen is disposed during inspection.

An additional embodiment relates to a method for determining drift in a position of a light beam with respect to a chuck on which a specimen is disposed during inspection. One embodiment of such a method is illustrated in FIG. 6. Many of the steps shown in FIG. 6 are not essential to practice of the method. In particular, one or more steps may be omitted from or added to the method shown in FIG. 6, and the method can still be practiced within the scope of this embodiment. In addition, many of the steps shown in FIG. 6 do not have to be performed in the order shown in FIG. 6 unless otherwise noted herein.

The method includes illuminating a surface with the light beam. The surface has a predetermined position with respect to the chuck during illumination, as shown in step 86. The surface may include a surface of a fiduciary. The fiduciary may be configured as described further herein. Alternatively, the surface may include a surface of a detector. In another alternative, the surface may include a surface of a mask positioned in front of a detector.

The light beam may include an oblique incidence beam. Alternatively, the light beam may include a normal incidence beam. In addition, two different light beams may illuminate the surface sequentially or simultaneously. The chuck may be configured as described above. In addition, illumination of the surface may be performed as described above.

The method also includes generating signals responsive to illumination of the surface, as shown in step 88. Generating the signals may be performed as described further herein. The signals may be generated using any of the embodiments of the detectors described herein. In addition, the method includes determining drift in the position of the light beam with respect to the chuck using the signals, as shown in step 90. Determining the drift in the position of the light beam may be performed as described herein. The drift may include drift of the position of the light beam with respect to the chuck in the x and/or y directions.

In some embodiments, the method includes altering the position of the light beam with respect to the chuck based on the drift, as shown in step 92. The position of the light beam may be altered based on the drift as described further herein. In an additional embodiment, the method may include determining positions of defects detected on the specimen during the inspection based on the drift, as shown in step 94. The positions of the defects may be determined as described herein. In addition, the inspection may be performed as described herein.

In some embodiments, the method may be performed between calibration steps, which involve calibration of an inspection system that includes the light beam and the chuck. In this manner, the surface may be measured not only during calibration but also again at later intervals, and the beam position drift measurements may be determined from a comparison of the later measurements and the calibration measurements as described further herein. In this manner, the methods described herein for determining drift in the position of the light beam may be performed much more frequently than calibration. In addition, since the method may be performed relatively quickly, the method will not substantially reduce the throughput of an inspection system on which the method is performed. Furthermore, such frequent performance of the method will enable much more accurate defect positions to be determined, which is advantageous for at least the reasons set forth herein. Each of the embodiments of the method described above may include any other step(s) described herein.

Further modifications and alternative embodiments of various aspects of the invention may be apparent to those skilled in the art in view of this description. For example, methods and systems for determining drift in a position of a light beam with respect to a chuck are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for determining drift in a position of a light beam with respect to a chuck on which a specimen is disposed during inspection, comprising:
   illuminating a surface with the light beam, wherein the surface has a predetermined position with respect to the chuck during said illuminating;
   generating signals responsive to said illuminating; and
   determining the drift in the position of the light beam with respect to the chuck using the signals.

2. The method of claim 1, wherein the drift comprises drift in the position of the light beam with respect to the chuck in the x direction or the y direction.

3. The method of claim 1, wherein the drift comprises drift in the position of the light beam with respect to the chuck in x and y directions.

4. The method of claim 1, wherein the surface comprises a surface of a fiduciary, and wherein the fiduciary comprises at least one patterned feature.

5. The method of claim 1, wherein the surface comprises a surface of a fiduciary, and wherein the fiduciary comprises at least one patterned feature having a lateral extent in the y direction and substantially the same characteristics along the lateral extent.

6. The method of claim 1, wherein the surface comprises a surface of a fiduciary, wherein the fiduciary comprises first and second patterned features, wherein the first patterned feature extends laterally in the y direction, and wherein the second patterned feature extends laterally in a direction at an angle to the y direction.

7. The method of claim 1, wherein the surface comprises a surface of a fiduciary, and wherein the fiduciary comprises a reflector having a three-dimensional shape.

8. The method of claim 1, wherein the surface comprises a surface of a detector.

9. The method of claim 1, wherein the surface comprises a surface of a mask positioned in front of a detector.

10. The method of claim 1, further comprising performing the method between calibrations of an inspection system that comprises the light beam and the chuck.

11. The method of claim 1, wherein the light beam comprises an oblique incidence beam.

12. The method of claim 1, wherein the light beam comprises a normal incidence beam.

13. The method of claim 1, further comprising altering the position of the light beam with respect to the chuck based on the drift.

14. The method of claim 1, further comprising determining positions of defects detected on the specimen during the inspection based on the drift.

15. A system configured to inspect a specimen and to determine drift in a position of a light beam with respect to a chuck on which the specimen is disposed during inspection, comprising:
   an illumination subsystem configured to illuminate a fiduciary with the light beam, wherein the fiduciary has a predetermined position with respect to the chuck during illumination;
   a detector configured to generate signals responsive to the illumination; and
   a processor configured to use the signals to determine the drift in the position of the light beam with respect to the chuck.

16. The system of claim 15, wherein the drift comprises drift in the position of the tight beam in the x direction or the y direction.

17. The system of claim 15, wherein the drift comprises drift in the position of the light beam in x and y directions.

18. The system of claim 15, wherein the fiduciary comprises at least one patterned feature.

19. The system of claim 15, wherein the fiduciary comprises at least one patterned feature having a lateral extent in the y direction and substantially the same characteristics along the lateral extent.

20. The system of claim 15, wherein the fiduciary comprises first and second patterned features, wherein the first patterned feature extends laterally in the y direction, and wherein the second patterned feature extends laterally in a direction at an angle to the y direction.

21. The system of claim 15, wherein the fiduciary comprises a reflector having a three-dimensional shape.

22. The system of claim 15, wherein the processor is further configured to use the drift to determine positions of defects detected on the specimen by the system.

23. The system of claim 15, wherein the processor is further configured to use the drift to alter the position of the light beam with respect to the chuck.

24. A system configured to inspect a specimen and to determine drift in a position of a light beam with respect to a chuck on which the specimen is disposed during inspection, comprising:

an illumination subsystem configured to illuminate a detector with the light beam, wherein the detector has a predetermined position with respect to the chuck during illumination, and wherein the detector is configured to generate signals responsive to the position of the light beam during the illumination; and a processor configured to use the signals to determine the drift in the position of the light beam with respect to the chuck.

25. The system of claim 24, wherein the drift comprises drift in the position of the light beam in the x direction or the y direction.

26. The system of claim 24, wherein the drift comprises drift in the position of the light beam in x and y directions.

27. The system of claim 24, wherein the detector is not configured for use in the inspection.

28. The system of claim 24, further comprising a mask positioned between the illumination subsystem and the detector such that the signals are further responsive to illumination of the mask by the light beam.

29. The system of claim 28, wherein the detector comprises a photodiode.

* * * * *